(12) United States Patent
Woo et al.

(10) Patent No.: US 12,053,269 B2
(45) Date of Patent: Aug. 6, 2024

(54) ELECTRODE BELT DEVICE FOR MEASURING BIO-SIGNAL

(71) Applicant: BILAB CO., LTD., Seocho-gu Seoul (KR)

(72) Inventors: Eung Je Woo, Bundang-Gu (KR); Tong In Oh, Hwaseong-si (KR)

(73) Assignee: BILAB CO., LTD. (KR)

( * ) Notice: Subject to any disclaimer, the term of this patent is extended or adjusted under 35 U.S.C. 154(b) by 785 days.

(21) Appl. No.: 16/465,964

(22) PCT Filed: Dec. 1, 2017

(86) PCT No.: PCT/KR2017/013988
§ 371 (c)(1),
(2) Date: May 31, 2019

(87) PCT Pub. No.: WO2018/101786
PCT Pub. Date: Jun. 7, 2018

(65) Prior Publication Data
US 2019/0298219 A1    Oct. 3, 2019

(30) Foreign Application Priority Data

Dec. 2, 2016 (KR) .......... 10-2016-0163296
Jul. 7, 2017 (KR) .......... 10-2017-0086203

(51) Int. Cl.
*A61B 5/00* (2006.01)
*A61B 5/053* (2021.01)
(Continued)

(52) U.S. Cl.
CPC .............. *A61B 5/0536* (2013.01); *A61B 5/00* (2013.01); *A61B 5/053* (2013.01); *A61B 5/0531* (2013.01);
(Continued)

(58) Field of Classification Search
CPC ......... A61B 5/0536; A61B 5/00; A61B 5/053; A61B 5/0531; A61B 5/6831;
(Continued)

(56) References Cited

U.S. PATENT DOCUMENTS

| 7,206,630 B1 | 4/2007 | Tarler |
| 9,060,705 B2 | 6/2015 | Holzhacker et al. |

(Continued)

FOREIGN PATENT DOCUMENTS

| CN | 103315722 A | 9/2013 |
| CN | 103547214 A | 1/2014 |

(Continued)

OTHER PUBLICATIONS

Netakeya Satoshi, "Electric Impedance Tomography Measuring Device", Dec. 2014, JP 2014233619, Translation (Year: 2014).*

(Continued)

*Primary Examiner* — Adam Z Minchella
(74) *Attorney, Agent, or Firm* — Renaissance IP Law Group LLP

(57) ABSTRACT

Disclosed is a fabric electrode belt for measuring a biometric signal. The fabric electrode belt for measuring a biometric signal according to an embodiment of the disclosure includes: a belt body unit including a stretchable material, and provided with electrodes to be in contact with a subject to be examined; and a circuit unit coupled to the belt body unit and configured to receive an electric signal based on impedance of a subject to be examined, measured by the electrodes, the circuit unit being disposed between the belt body units.

10 Claims, 18 Drawing Sheets

(51) Int. Cl.
*A61B 5/0531* (2021.01)
*A61B 5/0536* (2021.01)
*A61B 5/24* (2021.01)
*H05K 1/02* (2006.01)
*H05K 1/09* (2006.01)
*H05K 1/14* (2006.01)

(52) U.S. Cl.
CPC ......... *A61B 5/6831* (2013.01); *H05K 1/0283* (2013.01); *H05K 1/09* (2013.01); *H05K 1/147* (2013.01); *A61B 2562/164* (2013.01); *A61B 2562/227* (2013.01)

(58) Field of Classification Search
CPC ........ A61B 2562/164; A61B 2562/227; A61B 5/6823; A61B 5/25; A61B 2560/04; H05K 1/0283; H05K 1/09; H05K 1/147
See application file for complete search history.

(56) References Cited

U.S. PATENT DOCUMENTS

| | | | |
|---|---|---|---|
| 2005/0148887 A1 | 7/2005 | Reiter et al. | |
| 2006/0084855 A1 | 4/2006 | Teschner et al. | |
| 2008/0288026 A1* | 11/2008 | Cross | A61B 5/6833 607/60 |
| 2009/0048540 A1* | 2/2009 | Otto | A61B 5/1118 600/595 |
| 2009/0234244 A1* | 9/2009 | Tanaka | A61B 5/0536 600/547 |
| 2010/0049027 A1 | 2/2010 | Teschner et al. | |
| 2011/0015498 A1 | 1/2011 | Mestrovic et al. | |
| 2012/0246795 A1* | 10/2012 | Scheffler | A61B 5/0205 2/243.1 |
| 2016/0270700 A1* | 9/2016 | Baxi | A61B 5/6802 |

FOREIGN PATENT DOCUMENTS

| | | |
|---|---|---|
| CN | 103930021 A | 7/2014 |
| EP | 3017758 A1 | 11/2016 |
| JP | 2006187615 A | 7/2006 |
| JP | 2007502675 A | 2/2007 |
| JP | 3153409 U | 9/2009 |
| JP | 2009261435 A | 11/2009 |
| JP | 2013183840 A | 9/2013 |
| JP | 2014233619 A * | 12/2014 |
| JP | 2015508314 A | 3/2015 |
| KR | 20100008371 A | 1/2010 |
| KR | 20110128646 A | 11/2011 |
| KR | 101449471 B1 | 10/2014 |
| WO | 2015196298 A1 | 12/2015 |
| WO | 2016177901 A1 | 11/2016 |

OTHER PUBLICATIONS

Satoshi, Nebuya, Translation of JP 2014233619 "Electric Impedance Tomography Measuring Device", Dec. 2014 (Year: 2014).*
Baysal, Ugur et al., "Single Camera Photogrammetry System for EEG Electrode Identification and Localization", Annals of Biomedical Engineering, vol. 38, No. 4, pp. 1539-1547, Apr. 2010.
European Extended Search Report for Application No. 17875611.0, mailed Jul. 21, 2020.
Malone, Emma et al., "Stroke type differentiation using spectrally constrained multifrequency EIT: evaluation of feasibility in a realistic head model", Physiological Measurement, Institute of Physics and Engineering in Medicine, vol. 35, No. 6, pp. 1051-1066, 2014.

* cited by examiner

ELECTRODE BELT DEVICE FOR MEASURING BIO-SIGNAL

TECHNICAL FIELD

The disclosure relates to an electrode belt apparatus for measuring a biometric signal, and more particularly to an electrode belt apparatus for measuring a biometric signal, which improves accuracy in measurement based on stable contact regardless of change in volume of a subject to be examined, and provides comfortable wearing sensation while maintaining measurement performance even though it is used for a long time.

BACKGROUND ART

In general, electrical impedance tomography (EIT) technology refers to technology that a plurality of electrodes are attached to a skin of a human body, an electric current is applied through some electrodes among them, voltage is measured through other electrodes attached to the skin, and an image is made based on resistivity inside the human body.

In such EIT, reliability of an apparatus is largely varied depending on convenient and stable connection between a plurality of electric wires and the electrode. Therefore, various researches have recently been continued to improve the reliability of the EIT.

Meanwhile, the plurality of electrodes used for the EIT may be given in the form of a belt on which two or more electrodes are arrayed for easy contact with a human body and maintenance. Further, conductive gel or glue applied to the circumference of the electrode for stable contact of the electrode may cause a problem of affecting measurement data or causing skin irritation or infection according to a target or part to be examined, when it is used for a long time.

DISCLOSURE

Technical Problem

The disclosure is to provide an electrode belt apparatus for measuring a biometric signal, which provides comfortable wearing sensation while maintaining measurement performance even though it is used for a long time.

Technical Solution

According to an embodiment of the disclosure, an electrode belt apparatus for measuring a biometric signal includes: a belt body unit including a stretchable material, and provided with electrodes to be in contact with a subject to be examined; and a circuit unit coupled to the belt body unit and configured to receive an electric signal based on impedance of a subject to be examined, measured by the electrodes, the circuit unit being disposed between the belt body units.

Further, the belt body unit and the circuit unit may be alternately connected to form a single body extended horizontally.

Further, the circuit unit may be disposed between the belt body units.

Further, the circuit unit may be coupled to both ends of the belt body unit.

Further, the belt body unit may include: an electrode layer configured to become in contact with a subject to be examined, and including the electrodes of electric conductive fabric; a circuit layer coupling with the electrode layer, and electrically connected to the electrodes; and a cover layer coupling with the circuit layer, and including markers formed to have a plurality of colors and patterns respectively corresponding to the electrodes.

Further, at least one among the electrode layer, the circuit layer, and the cover layer may include a stretchable elastic material.

Further, a contact element for electric contact between the electrodes and the circuit layer may be formed between the electrode layer and the circuit layer, and the contact element may include conductive glue or thermo-compression bonding.

Further, the electrodes may be arranged at regular intervals, and the electrodes may be electrically connected to the belt body unit by one of an eyelet, conductive glue, and stitching.

Further, the circuit layer may include a conductive yarn for power connection between the electrodes and the circuit unit.

Further, the conductive yarn may be wired having a zigzag embroidery pattern on the circuit layer.

Further, the conductive yarn may be wired by stitching to be partially fixed on the circuit layer and have a length corresponding to a stretchable range of the belt body unit.

Further, the circuit unit may include a nonelastic material.

Further, the circuit unit may include a flexible printed circuit board (PCB).

Further, the circuit unit may supply an electric current to the electrodes and measure a voltage signal based on impedance of a subject to be examined.

Further, the circuit unit may include a circuit configured to inject an electric current from an electrical impedance tomography (EIT) apparatus into a human body as connected to a certain electrode in the belt body unit.

Further, the circuit unit may include a plurality of differential amplification circuits to measure and amplify difference in a voltage signal between two certain electrodes among the electrodes.

Further, an analog signal of the current output circuit and the differential amplification circuit may be directly connected to an electrical impedance tomography (EIT) apparatus, or a demodulation result of an analog-digital conversion signal may be transmitted to a main processor to make an image based on internal conductivity and permittivity distribution of a subject to be examined.

Further, the electrode layer may include a contact surface provided with the electrodes to be in contact with a subject to be examined, and the cover layer may include an exposure surface opposite to the contact surface and including the markers respectively corresponding to the electrodes.

According to an embodiment of the disclosure, an electrode belt apparatus for measuring a biometric signal according to an embodiment of the disclosure includes: a belt body unit provided with electrodes to be in contact with a subject to be examined, including a circuit and wiring electrically connecting with the electrodes, and provided with markers formed respectively corresponding to the electrodes and having a plurality of colors and patterns; and a circuit unit coupling with the belt body unit, and configured to generate an analog signal for measuring impedance by receiving and amplifying an electric signal about impedance of a subject to be examined, measured by the electrodes, the belt body unit and the circuit unit being alternately connected to form a single body.

Further, the belt body unit may include a stretchable elastic material.

Further, the belt body unit may include a contact surface provided with the electrodes to be in contact with a subject to be examined, and an exposure surface opposite to the contact surface and including the markers respectively corresponding to the electrodes.

Further, the circuit unit may include a nonelastic material.

Further, the circuit unit may include a flexible PCB.

Further, the circuit unit may include a plurality of differential amplification circuits configured to measure and amplify difference in a voltage signal between the two certain electrodes among the electrodes.

Further, the analog signal may be directly connected to an EIT apparatus, or a demodulation result of an analog-digital conversion signal may be transmitted to a main processor to make an image based on internal conductivity and permittivity distribution of a subject to be examined.

According to an embodiment of the disclosure, an electrode belt apparatus for measuring a biometric signal includes: a belt unit mountable along a circumference of a subject to be examined; and a cable unit coupling with the belt unit, mountable along the circumference of the subject to be examined, and including a plurality of electrode elements configured to form internal current distribution based on contact with the subject to be examined and measure induced voltage, the belt unit including a material at least partially stretchable in a lengthwise direction, and the cable unit is foldable to be folded and unfolded in a lengthwise direction.

Further, the belt unit may include a silicon material or a fiber elastic tube material, and the cable unit may include at least one of a flexible printed circuit board (PCB) having a length to be foldable corresponding to a stretchable range of the belt unit, a fiber belt including a conductive yarn, and a conductive painted polymer substrate.

Further, the cable unit may include at least one of a flexible PCB extended in a lengthwise direction in parallel with the belt unit and shaped like a modularized belt provided with a plurality of spaced electrode elements to be in contact with the subject to be examined, a fiber belt including a conductive yarn, and a conductive painted polymer substrate.

Further, the belt unit may include a plurality of coupling projections spaced apart from each other along a lengthwise direction, and the cable unit may include a plurality of electrode elements spaced apart from each other along a lengthwise direction and exposed to an outside as coupled to the coupling projection, so that the belt unit and the cable unit can couple with each other.

Further, the belt unit may include a hollow internal space along a lengthwise direction, and the cable unit may be inserted in the internal space of the belt unit in a lengthwise direction.

Further, the belt unit may include a plurality of exposure holes through which the electrode elements of the cable unit inserted therein can be exposed.

Further, the cable unit may modularized into at least one measurement module with respect to the belt unit, and the at least one measurement module is connected to each other by a connection unit in a lengthwise direction.

Further, the connection unit includes an elastic material.

According to an embodiment of the disclosure, an electrode belt apparatus for measuring a biometric signal includes: at least one belt unit including a shape extended in a lengthwise direction to be mountable to a subject to be examined, and stretchable in a lengthwise direction; and at least one cable unit mountable along a circumference of the subject to be examined, and including at least one pair of electrode elements configured to become in contact with the subject to be examined along a lengthwise direction, form internal current distribution, and measure induced voltage, the cable unit being folded and unfolded in a lengthwise direction as coupled to the belt unit.

Further, the belt unit may include a silicon material or a fiber elastic tube material, and the cable unit may include at least one among a flexible printed circuit board (PCB) including the electrode element and a plurality of circuit parts including at least one of a nonflexible PCB piece, a flexible PCB piece, a piece of conductive paint printed on a silicon substrate, and a fiber substrate, which are electrically connectable to the electrode element and spaced apart from each other in a lengthwise direction, a fiber belt including a conductive yarn, and a conductive painted polymer substrate.

Further, the cable unit may include at least one coupling projection penetrating the belt unit, and the coupling projection may include an electrode including one of fiber, conductive polymer and metal materials for mechanical coupling and electric connection between the belt unit and the cable unit.

Further, the belt unit may include a hollow internal space, and the cable unit may have a length to be foldable corresponding to a stretchable range of the belt unit and is inserted in the internal space of the belt unit in a lengthwise direction.

Further, the belt unit may include a plurality of exposure holes through which the electrode element of the cable unit inserted therein can be exposed.

Further, the cable unit may be modularized into at least one measurement module couplable to the belt unit, and the at least one measurement module may be connected to each other by a connection unit in a lengthwise direction.

Further, the connection unit may include an elastic material.

Advantageous Effects

According to an embodiment of the disclosure, the electrode belt apparatus is formed with sections elastically transformable regardless of biotransformation at a target part of a subject to be examined, so that contact between the electrodes and the part targeted to be examined can be improved, thereby enhancing accuracy of measurement.

Further, the electrode belt apparatus for measuring the biometric signal is stretchable, and therefore used by a critical patient, baby or child who are susceptible to pressure on a skin, for a long time. Therefore, the electrode belt apparatus is applicable to a field of measuring a cardiopulmonary function, which requires monitoring for a long time, for example, a machine respiration monitoring apparatus targeted for a critical patient, an apnea monitoring apparatus for a baby or child, etc.

Further, the conductive yarn is wired to be partially fixed to the belt body unit, and therefore not only the elasticity of the belt body unit but also multiple signal/power connections are maintained even when the belt body unit is elastically transformed in its lengthwise direction.

Further, the circuit part includes differential amplification circuit to detect a difference between the voltages of two certain electrodes among the electrodes, thereby improving accuracy in an output amplification signal.

BEST MODE

Below, embodiments of the disclosure will be described with reference to accompanying drawings and content shown the accompanying drawings. However, the concept of the disclosure is not limited to such embodiments, and may be differently proposed through addition, change, deletion, etc. of an element without departing from the scope of the disclosure.

Figure 1:
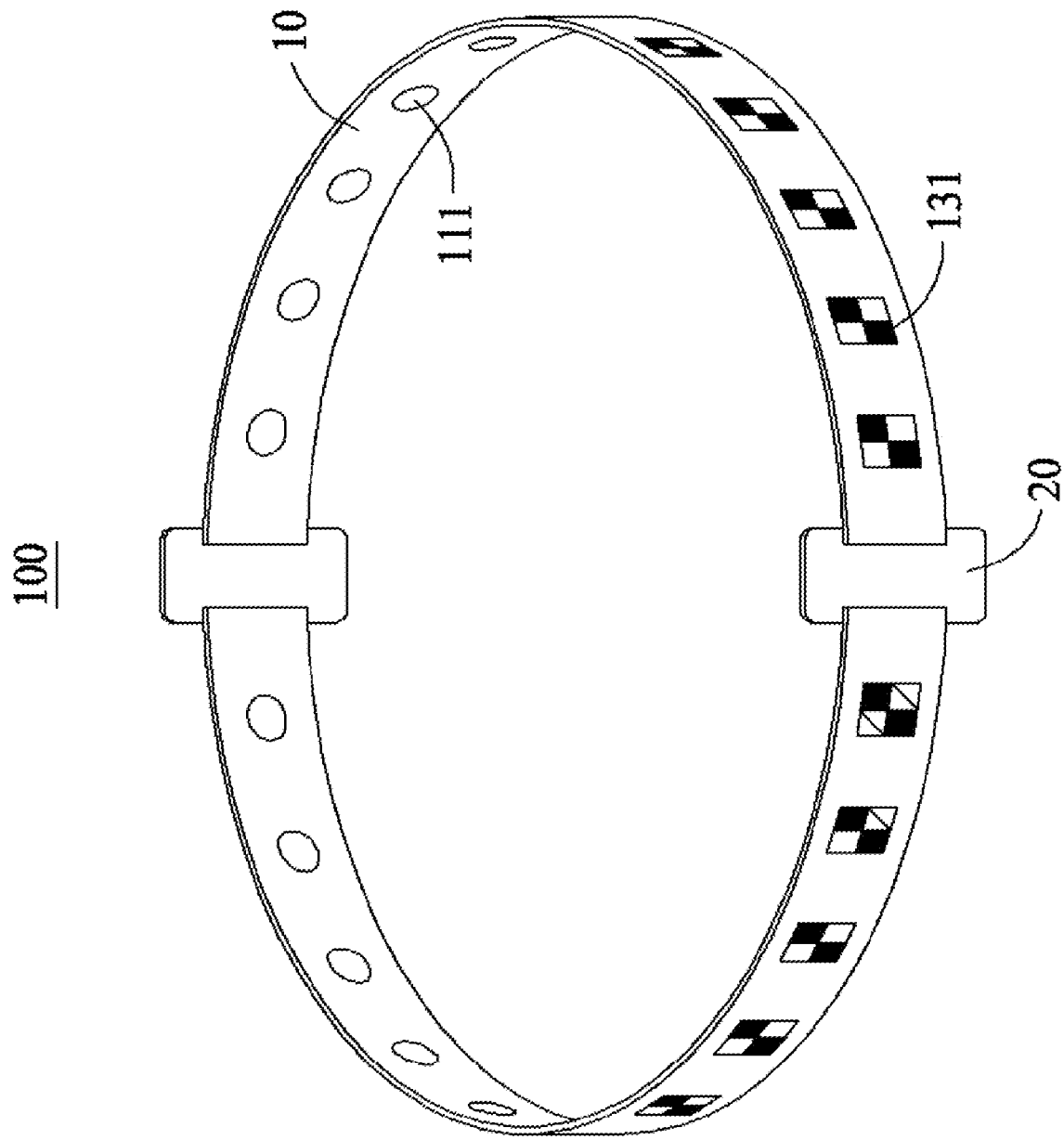
FIG. 1 is a perspective view of an electrode belt apparatus for measuring a biometric signal according to an embodiment of the disclosure.
Figure 2:
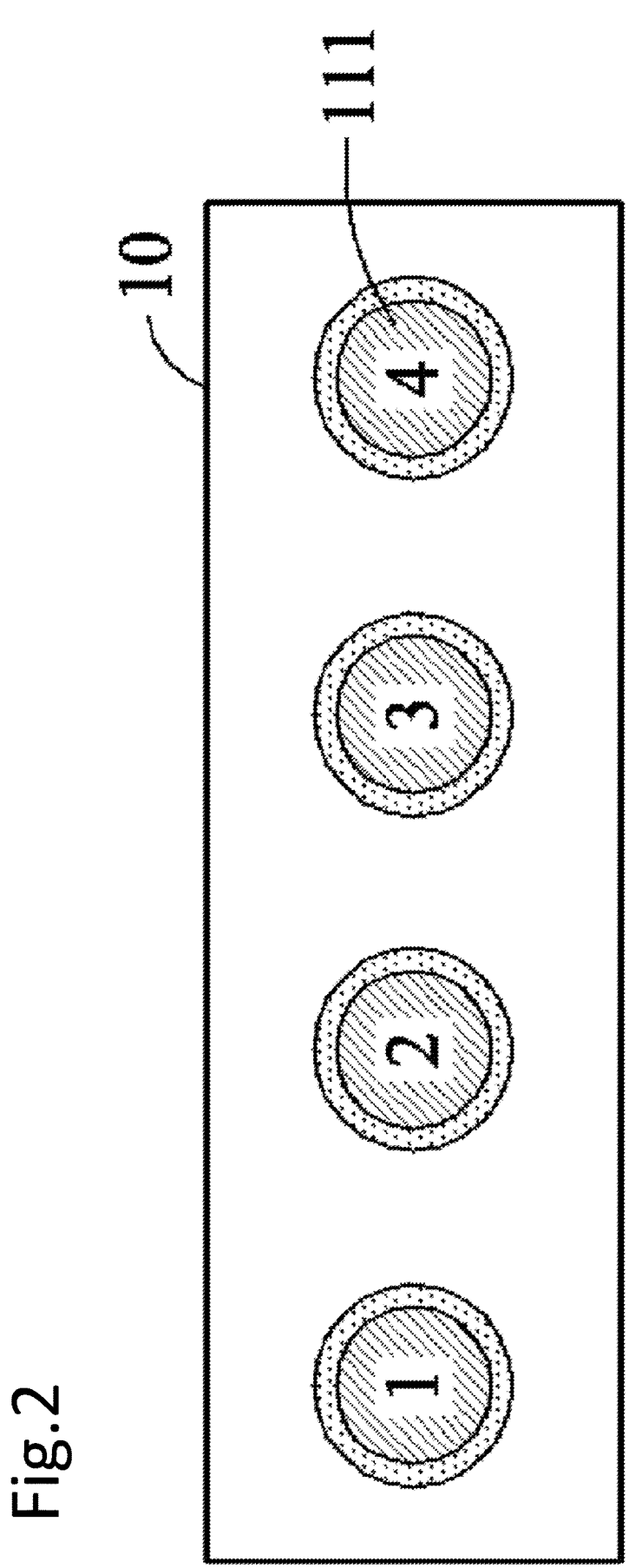
FIG. 2 is a top view of electrodes in an electrode belt apparatus for measuring a biometric signal according to an embodiment of the disclosure.
Figure 3:
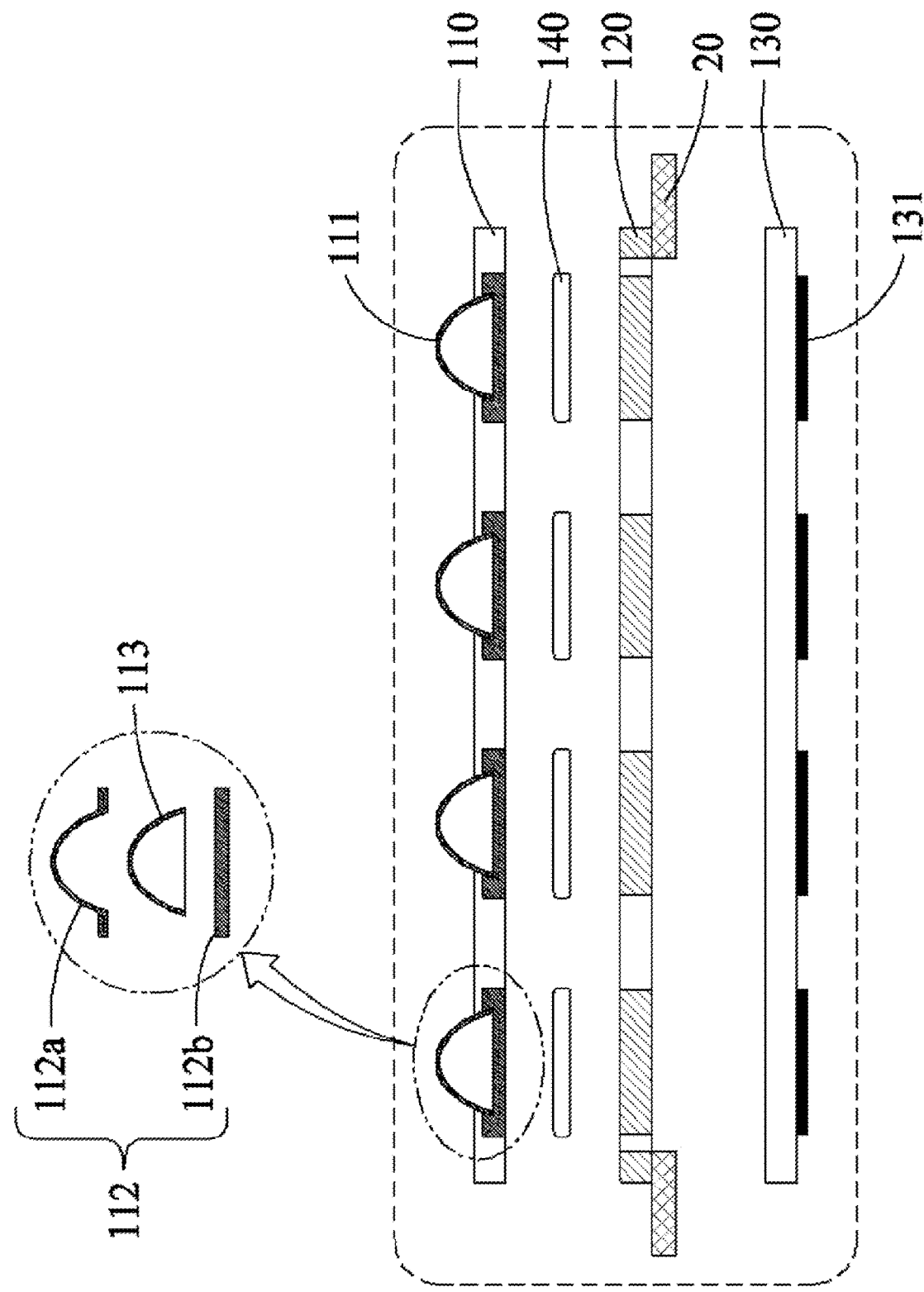
FIG. 3 is an exploded lateral cross-section view of an electrode belt apparatus for measuring a biometric signal according to an embodiment of the disclosure.
Figure 4:
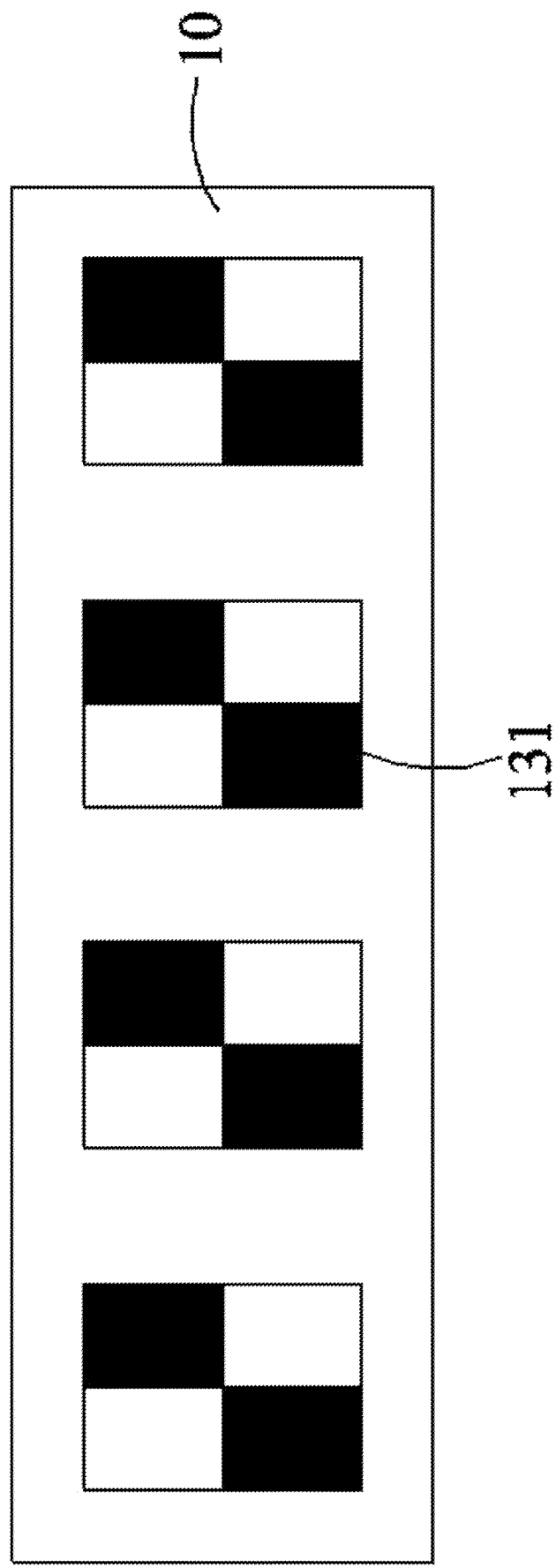
FIG. 4 is a top cross-section view of markers in an electrode belt apparatus for measuring a biometric signal according to an embodiment of the disclosure.
Figure 5:
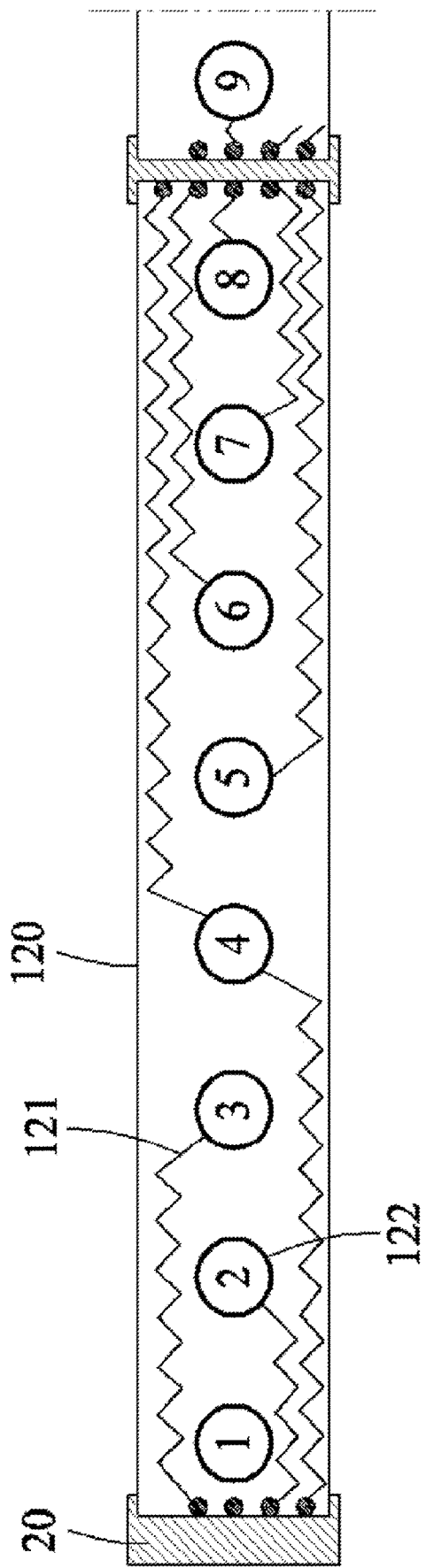
FIG. 5 is a cross-section view of a circuit layer in an electrode belt apparatus for measuring a biometric signal according to an embodiment of the disclosure.
Figure 6:
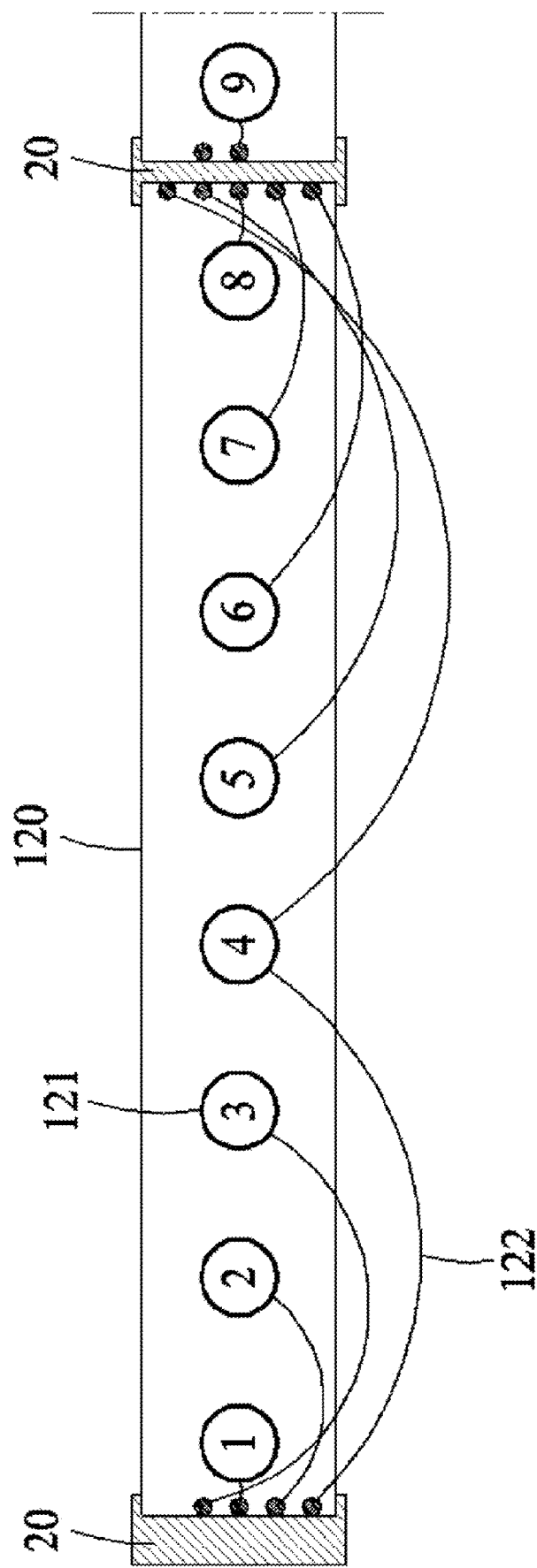
FIG. 6 illustrates that a conductive yarn is partially fixed to a circuit layer in an electrode belt apparatus for measuring a biometric signal according to an embodiment of the disclosure.

FIG. 1 is a perspective view of an electrode belt apparatus for measuring a biometric signal according to an embodiment of the disclosure, FIG. 2 is a top view of electrodes in an electrode belt apparatus for measuring a biometric signal according to an embodiment of the disclosure, FIG. 3 is an exploded lateral cross-section view of an electrode belt apparatus for measuring a biometric signal according to an embodiment of the disclosure, FIG. 4 is a top cross-section view of markers in an electrode belt apparatus for measuring a biometric signal according to an embodiment of the disclosure, FIG. 5 is a cross-section view of a circuit layer in an electrode belt apparatus for measuring a biometric signal according to an embodiment of the disclosure, and FIG. 6 illustrates that a conductive yarn is partially fixed to a circuit layer in an electrode belt apparatus for measuring a biometric signal according to an embodiment of the disclosure.

Referring to FIGS. 1 to 6, an electrode belt apparatus 100 for measuring a biometric signal according to an embodiment of the disclosure may include a belt body unit 10, and a circuit unit 20.

In general, the electrode belt apparatus 100 for measuring the biometric signal may be formed to have a structure mountable to a subject to be examined. For reference, the electrode belt apparatus 100 for measuring the biometric signal according to the disclosure may be applied to an electrical impedance tomography (EIT) apparatus, a machine respiration monitoring apparatus, an apnea monitoring apparatus, etc. and measures a biometric signal of a subject to be examined.

The belt body unit 10 may be provided with electrodes 111 that can contact a subject to be examined.

In more detail, the belt body unit 10 may include an electrode layer 110, a circuit layer 120, and the cover layer 130. Preferably, the electrode layer 110, the circuit layer 120, and the cover layer 130 may be made of a flexible elastic material (ex. fiber, silicon, rubber, etc.).

The electrode layer 110 may be in contact with a subject to be examined, and include electrodes 111 made of an electric conductive fabric. In this case, the electrode layer 110 may have a contact surface provided with the electrodes 111 and contacting a subject to be examined. Preferably, the contact surface may be made of an elastic material protected against friction due to contact with a subject to be examined.

The electrodes 111 provided in the electrode layer 110 may include an electrode structure 113, and a conductive fiber 112 surrounding the electrode structure 113.

For example, the electrode structure 113 may have one convex side and the other flat side shaped like a semicircle, and the conductive fibers 112a and 112b shaped corresponding to the shape of the electrode structure 113 and surrounding the surface of the electrode structure 113 (see FIG. 3).

Further, the electrodes 111 may be arrayed on the electrode layer 110 at regular intervals. For example, the electrodes 111 may be electrically connected to the belt body unit 10 by one of an eyelet, conductive glue, and stitching. In this case, for the connection with the electrodes 111, the belt body unit 10 may be formed with one of the eyelet, the conductive glue, and the stitching. In other words, the electrodes 111 may be variously fixed to the belt body unit 10 according to their kinds.

The circuit layer 120 may couple with the electrode layer 110, and have wiring and circuits for electric connection with the electrodes 111. In this case, a contact element 140 may be further provided between the electrode layer 110 and the circuit layer 120, and the contact element 140 may electrically connect the electrodes 111 and electric contact point 122 (to be described later). For example, a contact element 240 may include conductive glue or thermo-compression bonding.

The circuit layer 120 may include a conductive yarn 121 for power connection between the electrodes 111 and the circuit unit 20 (to be described later).

In more detail, the circuit layer 120 may include an electric contact point 122 at a position corresponding to each of the electrodes 111, and the conductive yarn 121 may be provided for electric connection between the electric contact point 122 and the circuit unit 20 (see FIG. 5 or 6).

For example, the conductive yarn 121 may be wired having a zigzag embroidery pattern on the circuit layer 120 as shown in FIG. 5, or the conductive yarn 121 may be wired by the stitching to be partially fixed on the circuit layer 120 as shown in FIG. 6.

Particularly, in the case where the conductive yarn 121 is wired to be partially fixed on the circuit layer 120, it is advantageous to achieve multiple signal/power connections while keeping the elasticity of the belt body unit 10 when the belt body unit 10 is elastically transformed in its lengthwise direction. Preferably, the conductive yarn 121 may be wired to have a length corresponding to a stretchable range of the belt body unit 10.

In more detail, when the electrode belt apparatus 100 for measuring the biometric signal is mounted to a subject to be examined, the belt body unit 10 may be transformed in its lengthwise direction elastic by change in volume due to vivo activity of a subject to be examined. In this case, the conductive yarn 121 wired to be partially fixed to the belt body unit 10 is not snapped but keeps a connected state on the belt body unit 10, thereby stably measuring impedance of a subject to be examined.

The cover layer 130 may be coupled to the circuit layer 120, and include markers 131 formed to have a plurality of colors and patterns respectively corresponding to the electrodes 111. In this case, the cover layer 130 may have an exposure surface provided with the markers 131.

For example, an image capturing apparatus (ex. a 3D camera) (not shown) may be provided to capture an image of the markers 131 and obtain a 3D image, and the image capturing apparatus may output a 3D model image about a part of a subject to be examined, on which the electrode belt apparatus 100 is worn. In more detail, the image capturing apparatus may obtain 3D volume information about a target part of a subject to be examined from information about a 2D image including the markers 131 formed to have the plurality of colors and patterns, the actual sizes of which are known.

Meanwhile, the circuit unit 20 may be coupled to the belt body unit 10, and supply an electric current to the electrodes 111 to thereby measure a voltage signal based on impedance of a subject to be examined. For example, the circuit unit 20 and the belt body unit 10 may be coupled by the eyelet.

The circuit unit 20 may be made of a nonelastic material. For example, the circuit unit 20 may be provided as a flexible printed circuit board (PCB) having a switching line. However, the circuit unit 20 is not limited to the flexible PCB, and may be made of various nonelastic materials as long as it can involve the switching line and be not stretchable.

The circuit unit 20 and the belt body unit 10 may be alternately arranged along their lengthwise directions. Referring to FIG. 1, two circuit units 20 are provided on one electrode belt apparatus 100 for measuring the biometric signal, but the circuit unit 20 is not limited to this structure and may have any structure where it can alternate with the belt body unit 10.

In other words, the belt body unit 10 and the circuit unit 20 are alternately connected to form a single body (i.e. the electrode belt apparatus 100). In more detail, the circuit unit 20 may be disposed between and coupled to the belt body units 10, or the circuit unit 20 may be coupled to both ends of the belt body unit 10.

The circuit unit 20 will be described in detail with reference to FIGS. 7 and 8.

Figure 7:
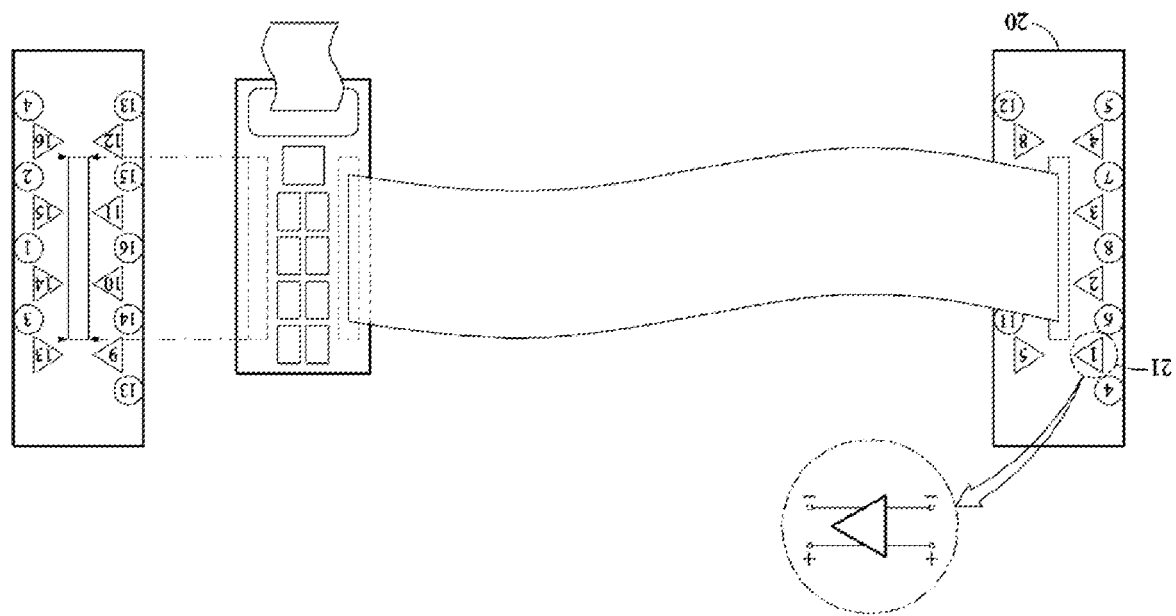
FIG. 7 illustrates a circuit part in an electrode belt apparatus for measuring a biometric signal according to an embodiment of the disclosure.
Figure 8:
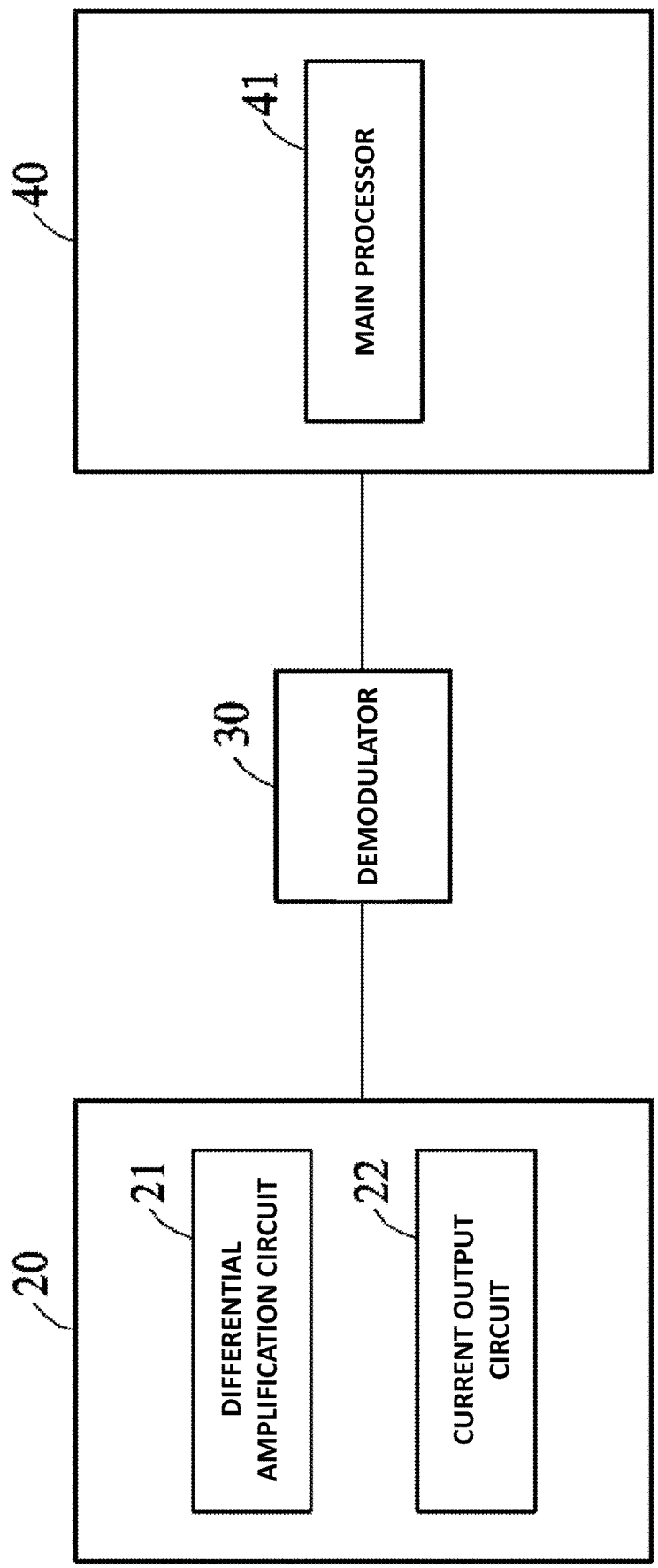
FIG. 8 is a block diagram schematically illustrating that an analog signal generated in a circuit part is transmitted to an electrical impedance tomography (EIT) system in an electrode belt apparatus for measuring a biometric signal according to an embodiment of the disclosure.

FIG. 7 illustrates a circuit part in an electrode belt apparatus for measuring a biometric signal according to an embodiment of the disclosure, and FIG. 8 is a block diagram schematically illustrating that an analog signal generated in a circuit part is transmitted to an EIT system in an electrode belt apparatus for measuring a biometric signal according to an embodiment of the disclosure.

Referring to FIGS. 7 and 8, an electrode belt apparatus 100 for measuring a biometric signal according to an embodiment of the disclosure may include a circuit unit 20.

The circuit unit 20 may be provided as a flexible PCB formed with a circuit line. In more detail, the circuit unit 20 may include a differential amplification circuit 21, and a current output circuit 22.

The differential amplification circuit 21 may serve to measure and amplify difference in a voltage signal between two certain electrodes among the electrodes 111.

The differential amplification circuit 21 employs a device excellent in common-mode rejection ratio (CMRR) performance, receives voltage signals of two certain electrodes among the electrodes 111 as inputs, and senses difference between the inputs (+, −), thereby improving accuracy of an output amplification signal.

Improvement in such CMRR performance play an important role in reducing measurement error and noise of the voltage signals of two certain electrodes among the electrodes 111, and may for example play a more important role in measuring a small change involved in a large impedance signal or amplifying electrocardiogram (ECG), electroencephalogram (EEG) and the like signals which involve a lot of noise and are very weak.

The current output circuit 22 may be connected to an EIT apparatus 40, and the current output through the current output circuit 22 is supplied to the electrodes 111 so that a voltage signal based on impedance of a subject to be examined can be measured. In this case, the voltage signal induced by the current output circuit 22 is measurable through the differential amplification circuit 21.

Specifically, the input/output analog signals (i.e. the amplified signal and the output current) of the differential amplification circuit 21 and the current output circuit 22 may be directly connected to the EIT apparatus 40.

Further, on the other hand, a demodulator 30 may be connected between the circuit unit 20 and the EIT apparatus 40 and transmit a demodulation result of an analog-digital conversion signal to a main processor 41, thereby making an image based on internal conductivity and permittivity distribution of a subject to be examined.

In this embodiment, the differential amplification circuit 21 and the current output circuit 22 for signal enhancement are provided on the circuit unit 20, but not limited thereto. Alternatively, the differential amplification circuit 21 and the current output circuit 22 may be directly attached on to the elastically-transformable belt body unit 10. In particular, when the differential amplification circuit 21 and the current output circuit 22 are directly attached to the belt body unit 10, circuit wiring may be achieved using the foregoing conductive yarn 121.

As described above, the electrode belt apparatus is formed with sections elastically transformable regardless of biotransformation at a target part of a subject to be examined, so that contact between the electrodes and the part targeted to be examined can be improved, thereby enhancing accuracy of measurement.

Further, the electrode belt apparatus for measuring the biometric signal is stretchable, and therefore used by a critical patient, baby or child who are susceptible to pressure on a skin, for a long time. Therefore, the electrode belt apparatus is applicable to a field of measuring a cardiopulmonary function, which requires monitoring for a long time, for example, a machine respiration monitoring apparatus targeted for a critical patient, an apnea monitoring apparatus for a baby or child, etc.

Further, the conductive yarn is wired to be partially fixed to the belt body unit, and therefore not only the elasticity of the belt body unit but also multiple signal/power connections are maintained even when the belt body unit is elastically transformed in its lengthwise direction.

Further, the circuit unit includes differential amplification circuit to detect a difference between the voltages of two certain electrodes among the electrodes, improving accuracy in an output amplification signal.

Figure 9:
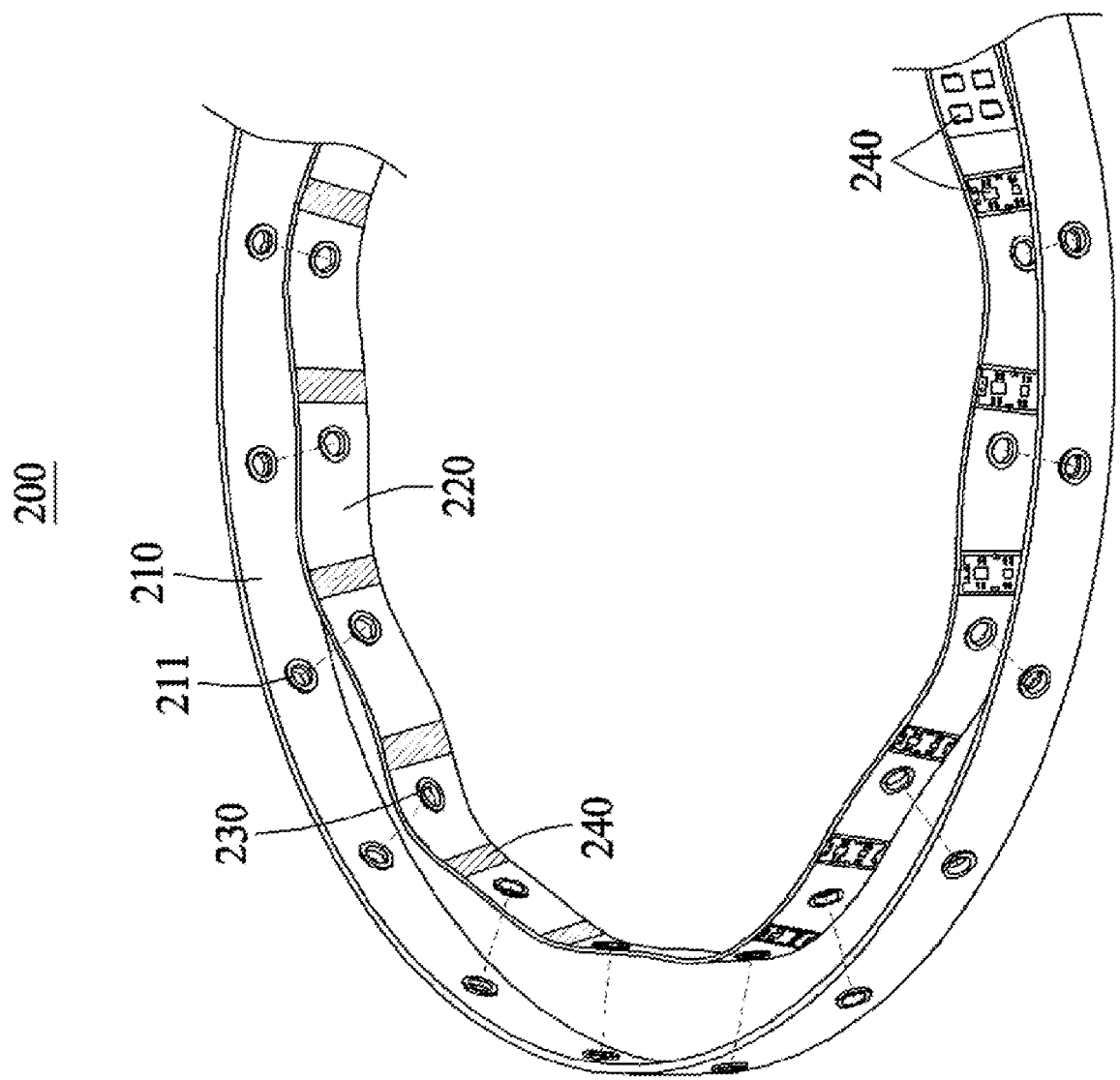
FIG. 9 is a perspective view of an electrode belt apparatus for measuring a biometric signal according to a second embodiment of the disclosure.
Figure 10:
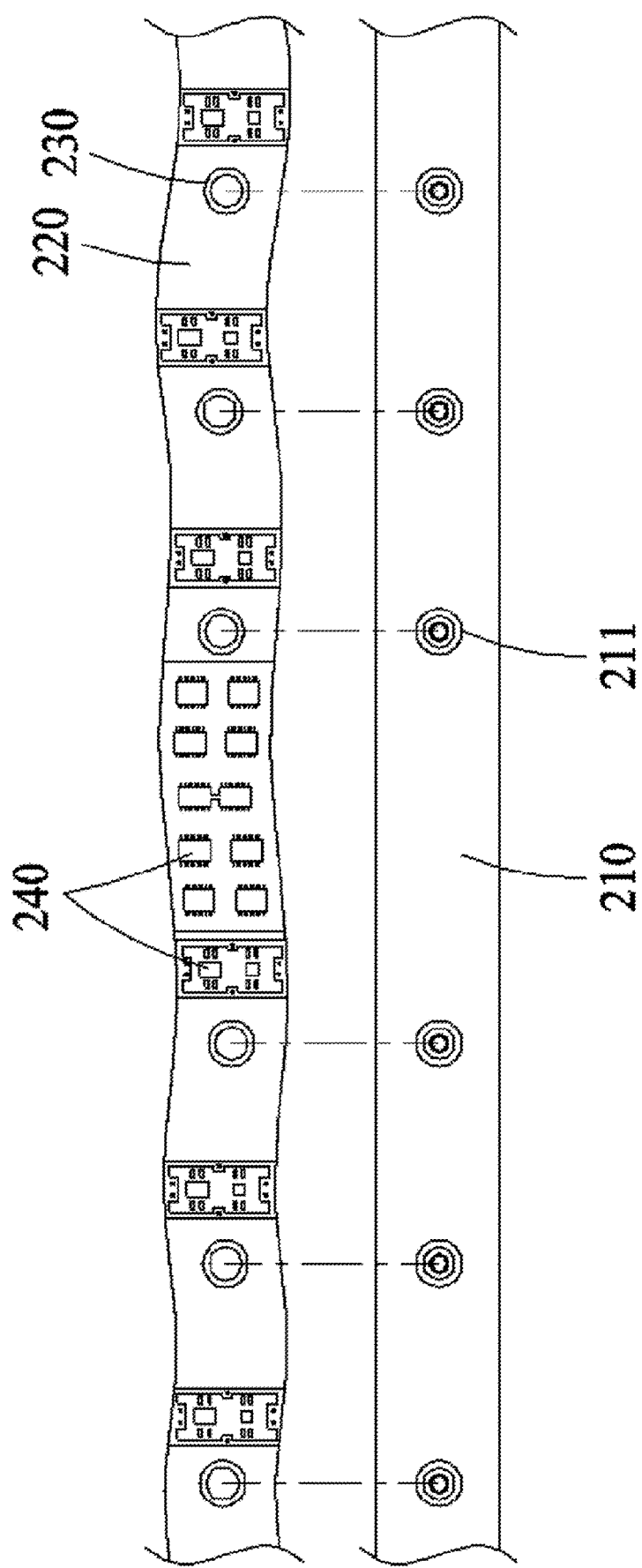
FIG. 10 is a schematic exploded plan view of the electrode belt apparatus for measuring the biometric signal, shown in FIG. 9.
Figure 11:
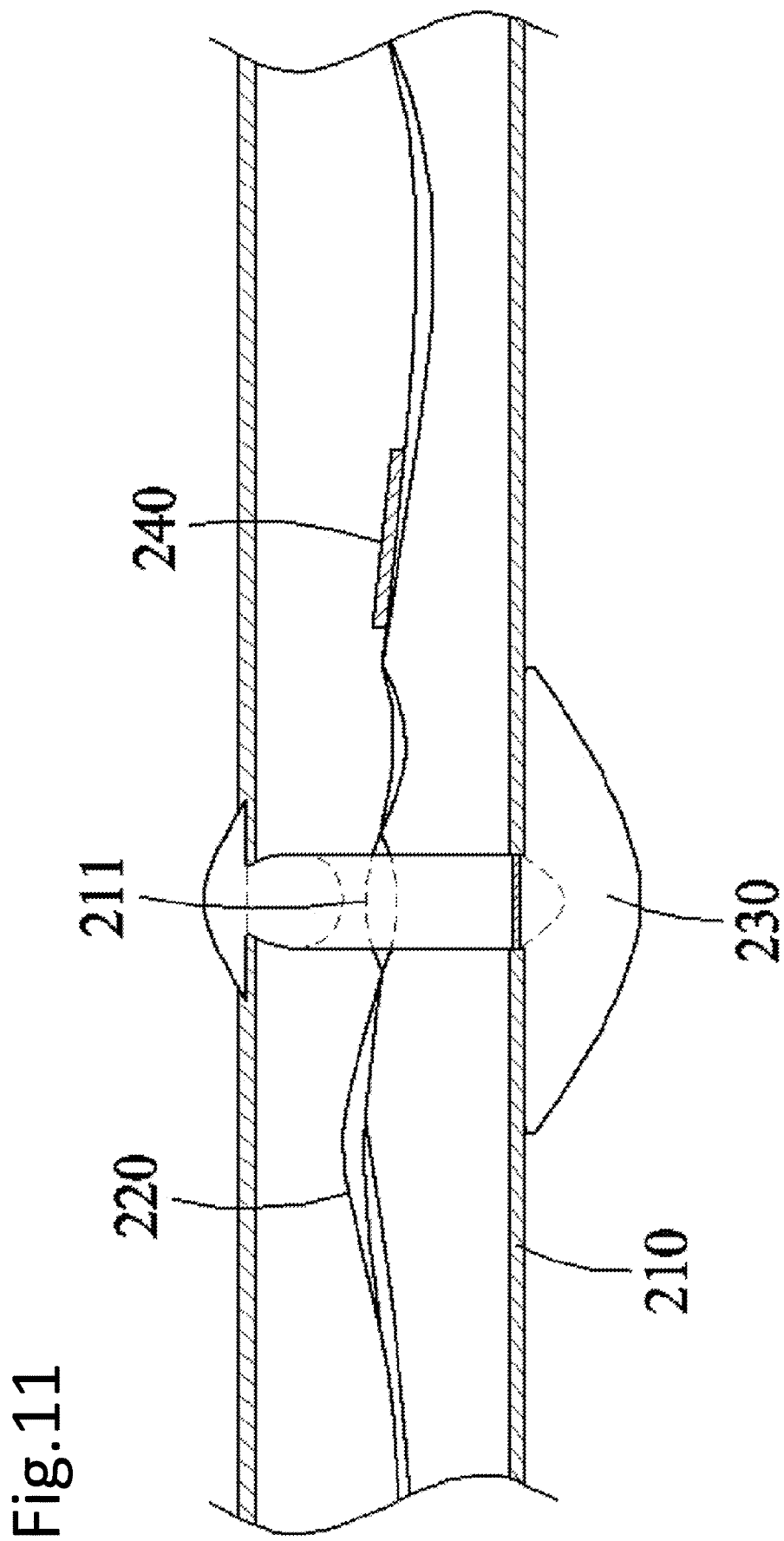
FIG. 11 is a schematic cross-section of the electrode belt apparatus for measuring the biometric signal, shown in FIG. 9.

FIG. 9 is a perspective view of an electrode belt apparatus for measuring a biometric signal according to a second embodiment of the disclosure, FIG. 10 is a schematic exploded plan view of the electrode belt apparatus for measuring the biometric signal, shown in FIG. 9, FIG. 11 is a schematic cross-section of the electrode belt apparatus for measuring the biometric signal, shown in FIG. 9, and FIG. is a schematic exploded plan view for explaining an operation state in which the electrode belt apparatus for measuring the biometric signal, shown in FIG. 10, is extended in a lengthwise direction.

Referring to FIG. 9, an electrode belt 200 apparatus for measuring a biometric signal according to the second embodiment of the disclosure includes a belt unit 210 and a cable unit 220.

The belt unit 210 is mountable along a circumference of a subject to be examined. The belt unit 210 is shaped like a band extendable in its lengthwise direction along an abdominal circumference of a subject to be examined. Further, the belt unit 210 is at least partially made of a flexible material so as to be stretchable in its lengthwise direction.

In this embodiment, the whole of the belt unit 210 is made of a stretchable elastic material, in more detail, a silicon material or a fiber elastic tube material. The belt unit 210 may be an elastic body protected against friction due to contact with a subject to be examined, and be soft to touch.

The belt unit 210 includes a plurality of coupling projections 211 for coupling with the cable unit 220 to be (described later). The coupling projection 211 may protrude toward the cable unit 220, and may be made of a conductive material. The features of the coupling projection 211 will be described in more detail along with the description about the features of the cable unit 220.

The cable unit 220 couples with the belt unit 210, is mountable along a circumference of a subject to be examined, and includes a plurality of electrode elements 230 for measuring the internal conductivity and permittivity distribution of the subject to be examined along the lengthwise direction. The cable unit 220 is shaped like a band extended in its lengthwise direction like the belt unit 210.

For reference, the cable unit 220 is not limited to the length of the illustrated example, and may be modularized as divided into a plurality of parts.

The cable unit 220 may connect with the belt unit 210 by the electrode element 230 as shown in FIG. 11. The plurality of electrode elements 230 may be provided corresponding to the number of coupling projections 211, couple with the coupling projections 211 made of a conductive material. The electrode element 230 may be coupled to the coupling projection 211 like a kind of hook, but the coupling is not limited to the hook coupling.

The cable unit 220 is a kind of flexible PCB made of a nonelastic material and provided with a control line. Further, the cable unit 220 is provided with a circuit part 240 electrically connectable with the electrode element 230. The plurality of electrode elements 230, which are spaced apart from each other, and the plurality of circuit parts 240, which are spaced apart from each other, are provided along the lengthwise direction of the cable unit 220.

Figure 12:
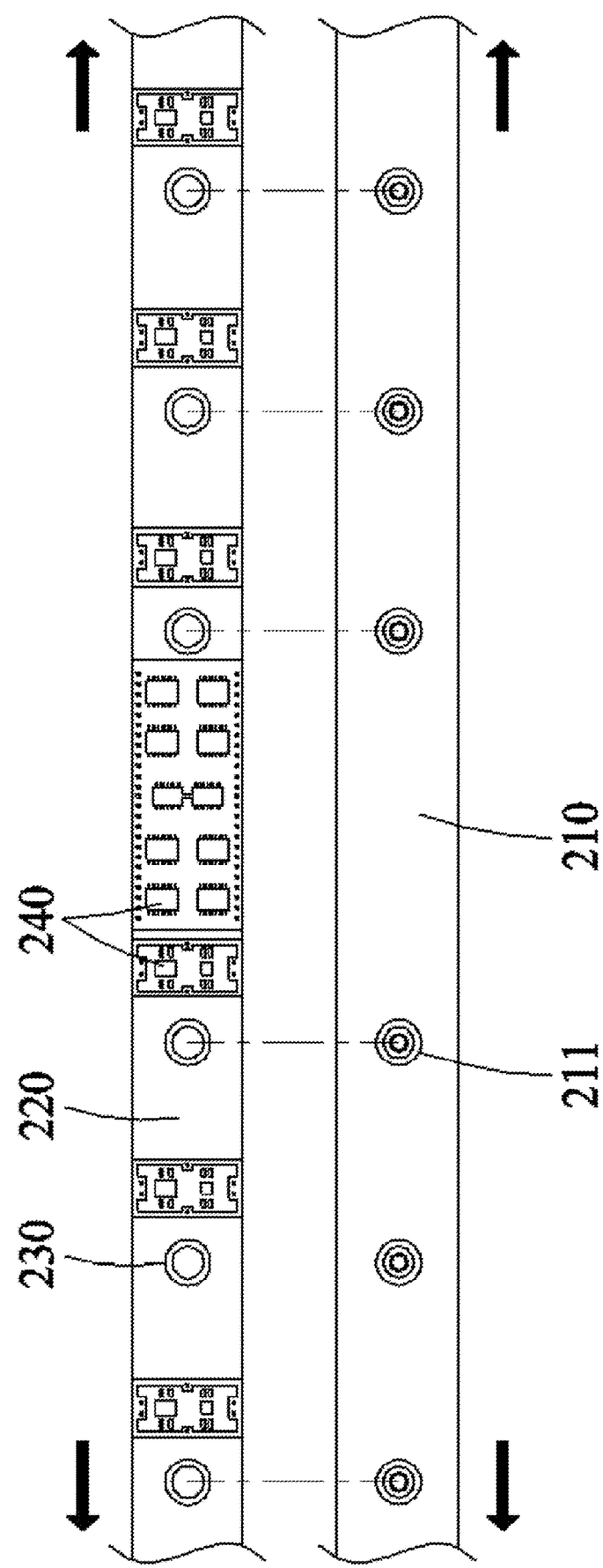
FIG. 12 is a schematic exploded plan view for explaining an operation state in which the electrode belt apparatus for measuring the biometric signal, shown in FIG. 10, is extended in a lengthwise direction.

Further, the cable unit 220 is provided as the nonelastic flexible PCB on the contrary to the elastic belt unit 210, and folded or unfolded in its lengthwise direction. Thus, as shown in FIGS. 10 and 12, the cable unit 220 is folded or unfolded as the belt unit 210 is stretched and contracted in its lengthwise direction, thereby keeping coupling with the belt unit 210. For reference, alternatively, the cable unit 220 may include at least one of a conductive painted polymer substrate and a fiber belt including a conductive yarn, as well as the flexible PCB.

Meanwhile, the cable unit 220 is made of the flexible PCB, and signal and control lines are connected to each other between the plurality of electrode elements 230 and between the circuit parts 240. In this case, there are at least one pair of electrode elements 230, i.e. two or more electrode elements 230, and therefore current distribution is formed based on the current applied to the electrode. In other words, it is possible to obtain internal conductivity and permittivity distribution of a subject to be examined based on distribution of voltage induced by at least one pair of electrode elements 230 among the plurality of electrode elements 230.

The circuit part 240 includes at least one of a nonflexible PCB provided in the vicinity of a coupling element of the electrode element 230, a flexible PCB piece, a piece of a silicon substrate printed with conductive paint, and a fiber substrate. The circuit part 240 provided as such a nonflexible PCB piece refers to a primary circuit for voltage measurement and current injection into the electrode element 230 provided on the cable unit 220 that is made of the flexible PCB and folded and unfolded.

For reference, although it is not illustrated in detail, the electrode element 230 provided along the lengthwise direction of the cable unit 220 including the flexible PCB may become in point-contact with a subject to be examined, via the belt unit 210. Such contact between the electrode element 230 and a subject to be examined may be variously changeable.

With the foregoing configuration, operation of an electrode belt apparatus 200 for measuring a biometric signal will be described with reference to FIGS. 10 to 12.

First, as shown in FIGS. 10 and 11, the coupling projection 211 of the belt unit 210 and the electrode element 230 of the cable unit 220 are coupled to each other, and thus both the belt unit 210 and the cable unit 220 are coupled without being extended in their lengthwise directions. In this case, the belt unit 210 and the cable unit 220 are coupled in the state that the cable unit 220 is longer than the belt unit 210, and therefore the cable unit 220 is partially folded in its lengthwise direction and coupled to the belt unit 210. Here, only the electrode element 230 of the cable unit 220 inside the belt unit 210 is exposed to the outside of the belt unit 210.

Then, the belt unit 210 and the cable unit 220 are mounted to an abdomen of a subject to be examined, as coupled to each other, and, as shown in FIG. 12, extended in its lengthwise direction due to change in the circumference or volume of the abdomen based on vivo activities such as breathing of the subject to be examined.

Specifically, the belt unit 210 made of a material stretchable in its lengthwise direction is transformed in its lengthwise direction elastic. In connection with the stretching, the cable unit 220 connected to the belt unit 210 is also unfolded in its lengthwise direction. Therefore, the electrode element 230 provided in the cable unit 220 is always in close-contact with a subject to be examined, regardless of the state of the subject to be examined, thereby measuring the impedance of the subject to be examined.

Figure 13:
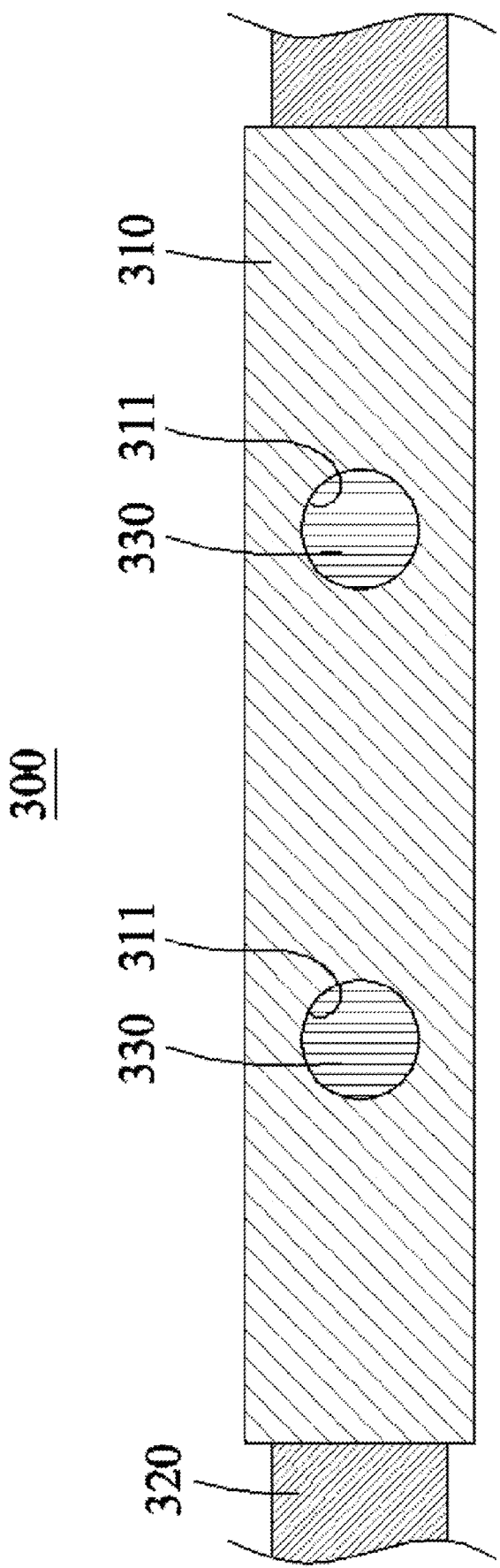
FIG. 13 is a schematic plan view of an electrode belt apparatus for measuring a biometric signal according to a third embodiment of the disclosure.
Figure 14:
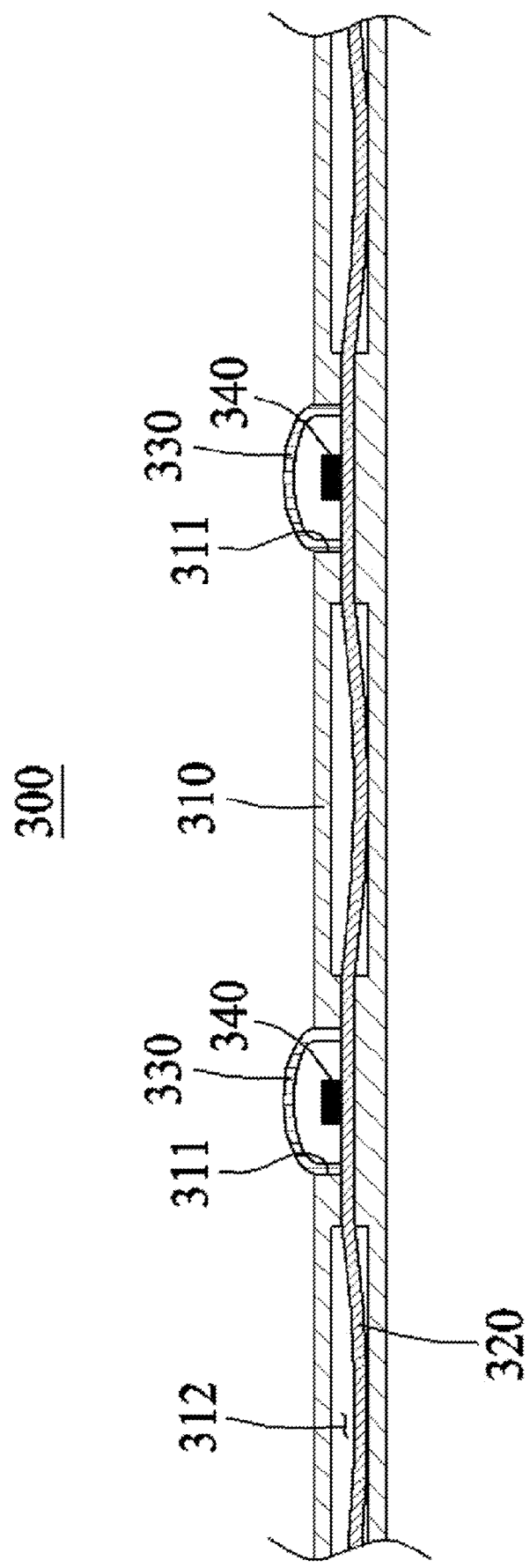
FIG. 14 is a schematic cross-section of the electrode belt apparatus for measuring the biometric signal, shown in FIG. 13.
Figure 15:
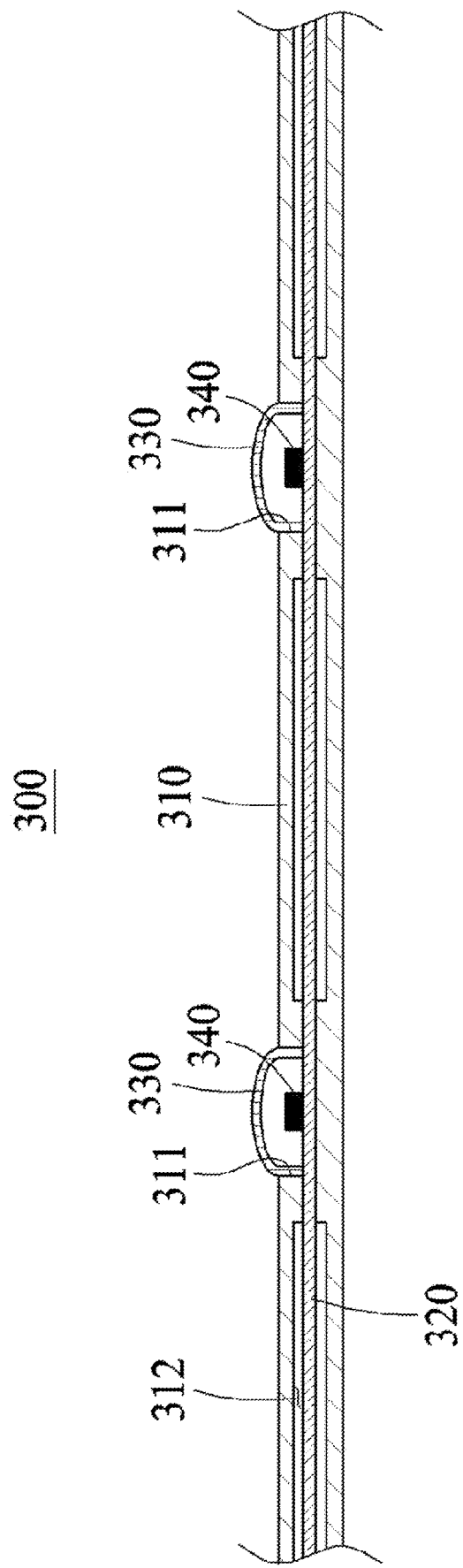
FIG. 15 is a schematic exploded cross-section view for explaining an operation state in which the electrode belt apparatus for measuring the biometric signal, shown in FIG. 14, is extended.

FIG. 13 is a schematic plan view of an electrode belt apparatus for measuring a biometric signal according to a third embodiment of the disclosure, FIG. 14 is a schematic cross-section of the electrode belt apparatus for measuring the biometric signal, shown in FIG. 13, and FIG. 15 is a schematic exploded cross-section view for explaining an operation state in which the electrode belt apparatus for measuring the biometric signal, shown in FIG. 14, is extended.

Referring to FIG. 13, an electrode belt apparatus 300 for measuring a biometric signal according to the third embodiment of the disclosure includes a belt unit 310 and a cable unit 320.

Here, the belt unit 310 is made of a material stretchable in its lengthwise direction, for example, a silicon material or a fiber elastic tube material, and the cable unit 320 is a kind of flexible PCB and includes an electrode element 330 and a circuit part (not shown). The features of the belt unit 310 and the cable unit 320 are similar to those of the second embodiment, and thus detailed descriptions thereof will be omitted.

Meanwhile, in the electrode belt apparatus 300 for measuring a biometric signal according to the third embodiment, the cable unit 320 is insertable in the belt unit 310 along the lengthwise direction. In other words, the belt unit 310 internally includes a hollow space 312 as shown in FIG. 14, and the cable unit 320 is inserted in the hollow space 312 in its lengthwise direction.

In this case, the cable unit 320 is provided as a flexible PCB, and the electrode element 330 electrically connectable with the flexible PCB is exposed through an exposure hole 311 provided in the belt unit 310. In other words, the electrode element 330 is provided as a kind of coupling projection to be coupled via the exposure hole 311 of the belt unit 310, and also has a function of applying an electric current. Therefore, the electrode element 330 exposed to the outside of the belt unit 310 becomes in contact with a subject to be examined, and measures voltage induced by forming the internal current distribution, thereby obtaining human body information about a subject to be examined.

For reference, the nonflexible PCB pieces, i.e. the circuit parts 240 (see FIGS. 1 to 4) in this embodiment is provided corresponding to the plurality of electrode elements 330 provided on one side of the flexible PCB, i.e. the cable unit 320. However, these features are the same as those of the second embodiment, and therefore detailed illustration and descriptions will be omitted.

With the foregoing configuration, an operation state of the electrode belt apparatus 300 for measuring a biometric signal 300 will be described with reference to FIGS. 14 and 15.

First, as shown in FIG. 14, the electrode element 330 of the cable unit 320 inserted in the internal space 312 of the belt unit 310 in its lengthwise direction is exposed through the exposure hole 311 of the belt unit 310. In this case, the cable unit 320 is in a folded state inside the internal space 312 of the belt unit 310.

When the belt unit 310 is extended in its lengthwise direction as shown in FIG. 15, the cable unit 320 inserted in the belt unit 310 is unfolded. Therefore, the cable unit 320 is unfolded as the belt unit 310 is stretched in its lengthwise direction, it is possible to flexibly cope with the contact of the electrode element 330 in accordance with change in abdomen volume of a subject to be examined.

Figure 16:
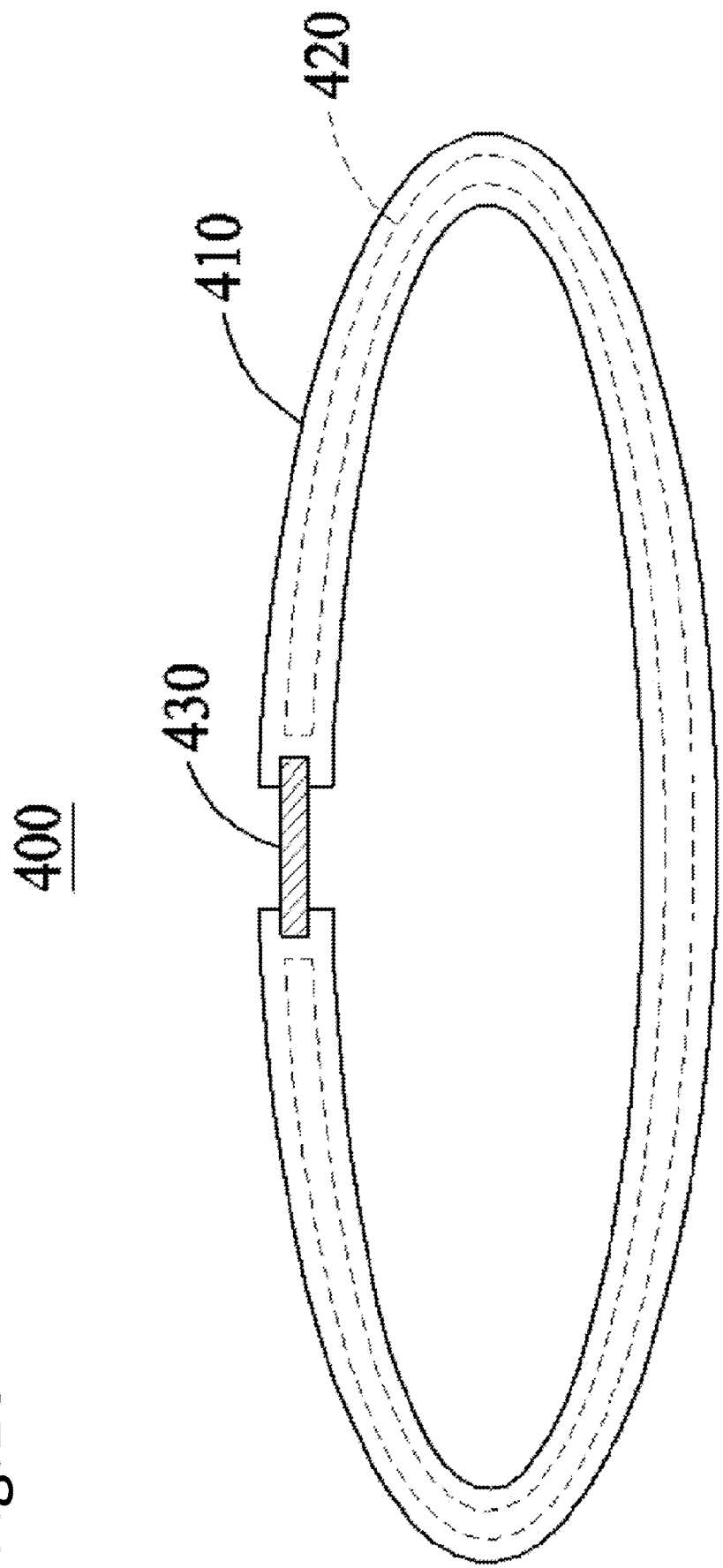
FIG. 16 is a schematic perspective view of an electrode belt apparatus for measuring a biometric signal according to a fourth embodiment of the disclosure.
Figure 17:
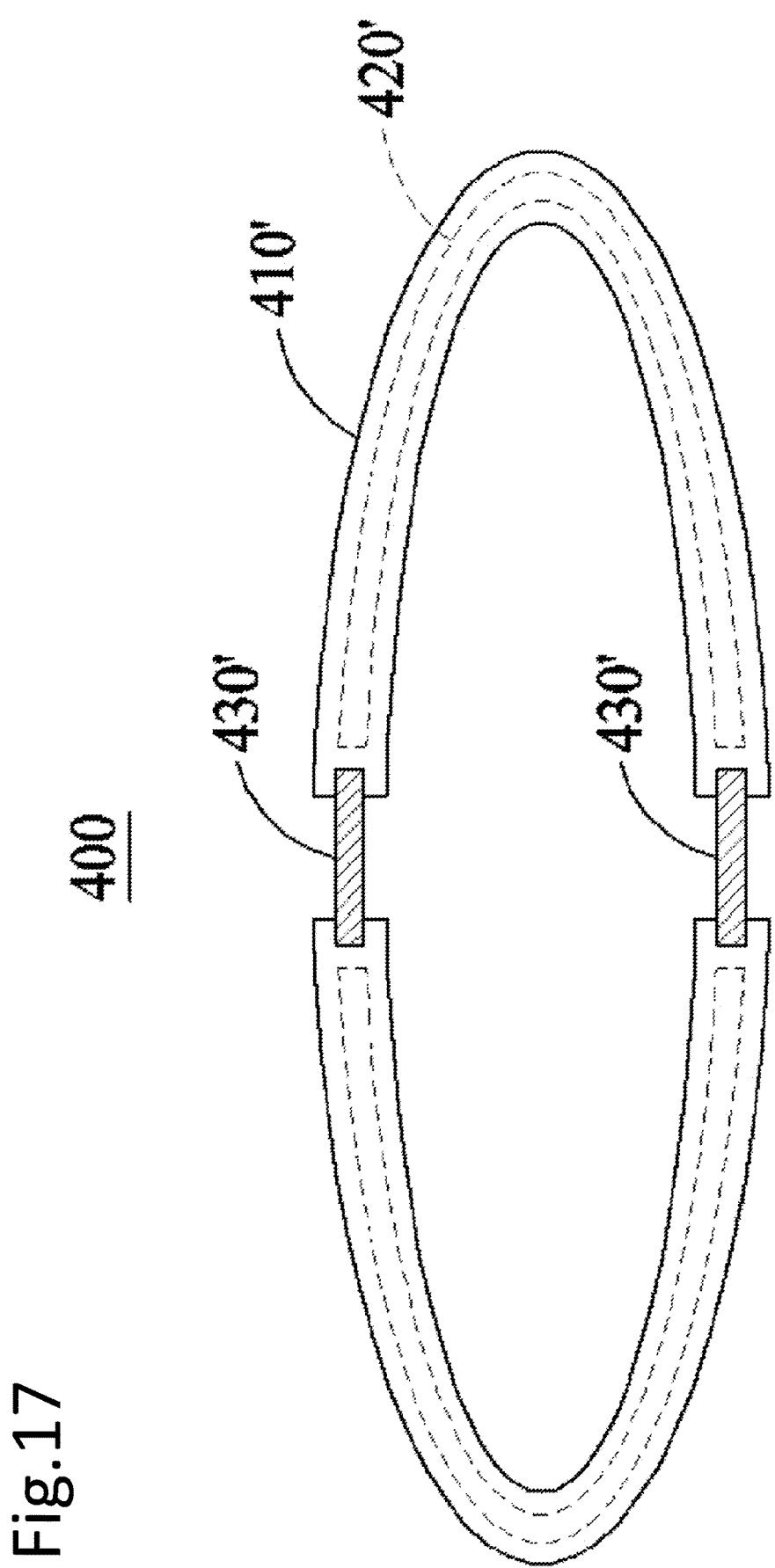
FIG. 17 is a perspective view schematically illustrating an alternative example of the electrode belt apparatus for measuring the biometric signal, shown in FIG. 16.
Figure 18:
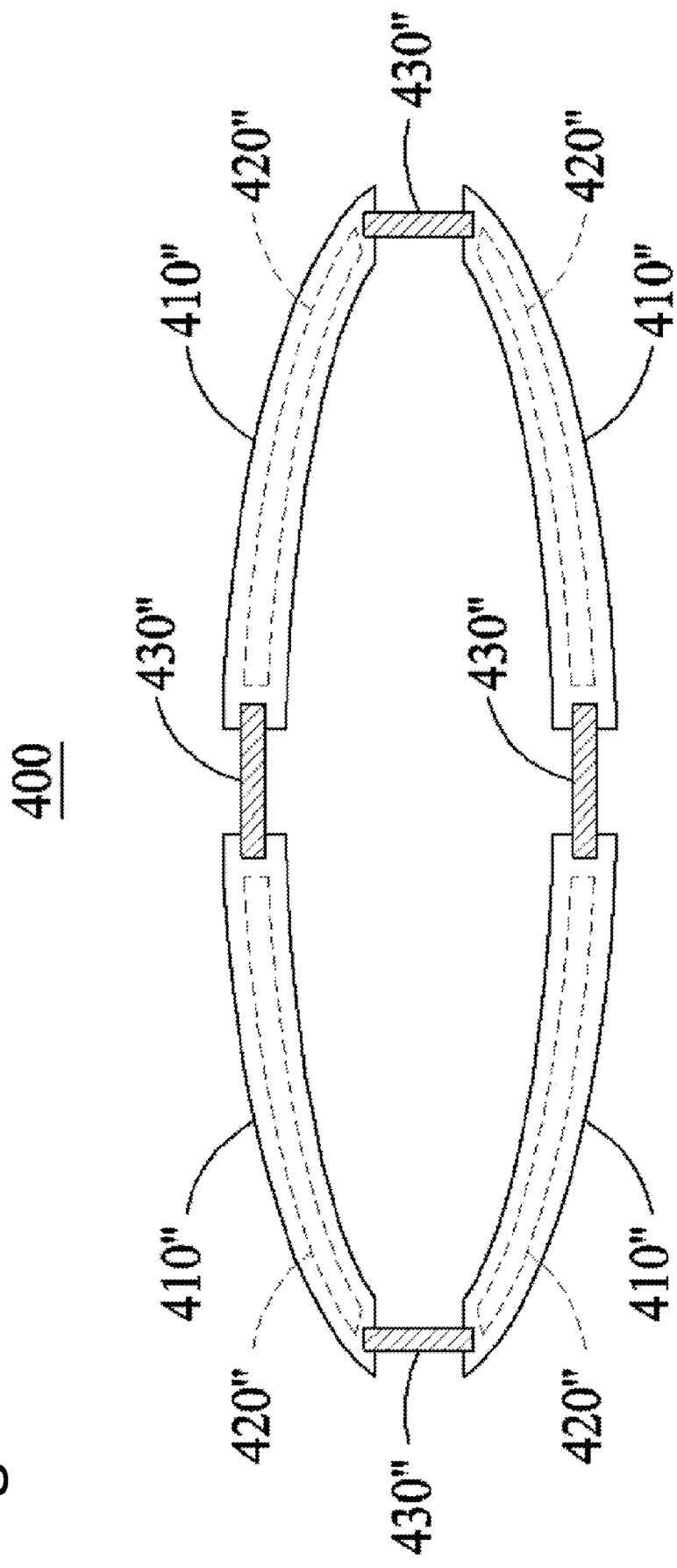
FIG. 18 is a perspective view schematically illustrating another alternative example of the electrode belt apparatus for measuring the biometric signal, shown in FIG. 16.

FIG. 16 is a schematic perspective view of an electrode belt apparatus for measuring a biometric signal according to a fourth embodiment of the disclosure, FIG. 17 is a perspective view schematically illustrating an alternative example of the electrode belt apparatus for measuring the biometric signal, shown in FIG. 16, and FIG. 18 is a perspective view schematically illustrating another alternative example of the electrode belt apparatus for measuring the biometric signal, shown in FIG. 16.

Referring to FIGS. 16 to 18, an electrode belt apparatus 400 for measuring a biometric signal according to the fourth embodiment of the disclosure is schematically illustrated. As shown in FIG. 16, the electrode belt apparatus 400 for measuring the biometric signal includes a belt unit 410, a cable unit 420, and a connection unit 430.

Like the third embodiment, the belt unit 410 is made of a silicon or fiber elastic tube stretchable in its lengthwise direction to cope with change in volume of a subject to be examined. Further, like the third embodiment, the cable unit 420 also includes a flexible PCB provided with an electrode element (not shown) and a circuit part (not shown) and is inserted in the belt unit 410 in its lengthwise direction. Here, the cable unit 420 may include at least one of a conductive painted polymer substrate and a fiber belt including a conductive yarn, and the belt unit 410 may be also made of the nonelastic material.

The cable unit 420 coupled to the belt unit 410 is modularized into at least one measurement module. FIG. 16 illustrates that the cable unit 420 is provided as one measure module and has one end and the other end connected each other by the connection unit 430.

Here, the connection unit 430 is made of a material transformable in its lengthwise direction like an elastic material, and configured to flexibly cope with change in volume of a subject to be examined in the state that the belt unit 410 and the cable unit 420 are coupled to each other.

Meanwhile, as shown in FIG. 17, alternatively, a cable unit 420' may be provided as two measurement modules coupled to each other, and thus connected by two connection units 430'. In addition, as shown in FIG. 10, a cable unit 420" may be provided as four measurement modules coupled to each other, and thus connected by four connection units 430".

In other words, the number of modularized measurement modules is not limited to those shown in FIGS. 8 to 10, and at least one measurement module may be provided and connected by the connection unit 430, 430', 430".

The disclosure is not limited by the foregoing embodiments but variously embodied within the appended claims. It will be appreciated that various changes can be made by a person having an ordinary skill in the art to which the disclosure pertains, without departing from the scope of the disclosure defined in the claims.

What is claimed is:

1. An electrode belt apparatus for measuring a biometric signal, comprising:
    at least one belt body unit, the at least one belt body unit provided with four or more electrodes placed for tomographic measurement at different positions from one end to the other to be in contact with a subject to be examined; and
    a circuit unit electrically coupled to each of the at least one belt body unit and configured to receive an electric signal based on impedance of a subject to be examined, measured by the electrodes,
    the circuit unit being disposed between and electrically coupled to different belt body units, or electrically coupled to opposite ends of a common belt body unit,
    wherein the circuit unit includes two ends, wherein the two ends of the circuit unit are electrically connected to the different belt body units, or are electrically connected to opposite ends of the common belt body unit,
    wherein the at least one belt body unit comprises:
        an electrode layer configured to be in contact with the subject to be examined;
        a circuit layer coupled to the electrode layer and electrically connected between the electrodes and each end of the circuit unit; and
        a cover layer coupled to the circuit layer,
        wherein a contact element, for electric contact between each of the electrodes and the circuit layer, is formed between the electrode layer and the circuit layer,
        wherein the at least one belt body unit and both ends of the circuit unit are alternately and electrically connected to form a single body extending horizontally, and
        wherein the circuit unit is configured to input and output analog signals directly from and to an electrical impedance tomography (EIT) apparatus.

2. The electrode belt apparatus for measuring the biometric signal according to claim 1, wherein:
    the electrode layer comprises the electrodes, wherein the electrodes comprise an electrically conductive fabric; and
    the cover layer comprises markers formed to have a plurality of colors and patterns respectively corresponding to the electrodes.

3. The electrode belt apparatus for measuring the biometric signal according to claim 1, wherein at least one among the electrode layer, the circuit layer, and the cover layer comprises a stretchable elastic material.

4. The electrode belt apparatus for measuring the biometric signal according to claim 1, wherein the contact element comprises conductive glue or thermo-compression bonding.

5. The electrode belt apparatus for measuring the biometric signal according to claim 1, wherein the circuit unit comprises a nonelastic material.

6. The electrode belt apparatus for measuring the biometric signal according to claim 1, wherein the circuit unit supplies an electric current to the electrodes and measures a voltage signal based on impedance of a subject to be examined.

7. The electrode belt apparatus for measuring the biometric signal according to claim 6, wherein the circuit unit comprises a plurality of differential amplification circuits to measure and amplify difference in a voltage signal between two certain electrodes among the electrodes and a current output circuit to output an electric current between the two certain electrodes among the electrodes.

8. The electrode belt apparatus for measuring the biometric signal according to claim 7, wherein the analog signals of the current output circuit and the differential amplification circuit is directly connected to the EIT apparatus.

9. The electrode belt apparatus for measuring the biometric signal according to claim 1, wherein the at least one belt body unit comprises a stretchable elastic material.

10. The electrode belt apparatus for measuring the biometric signal according to claim 1, wherein the circuit layer comprises a conductive yarn for power connection between the electric contact and each end of the circuit unit,
    wherein the conductive yarn has a length corresponding to a stretchable range of the at least one belt body unit, and
    wherein the conductive yarn is wired having a zigzag embroidery pattern or stitching to be partially fixed on the circuit layer.

* * * * *